United States Patent
Cabauy

(10) Patent No.: US 9,647,299 B2
(45) Date of Patent: May 9, 2017

(54) SMALL FORM FACTOR BETAVOLTAIC BATTERY FOR MEDICAL IMPLANTS

(71) Applicant: Peter Cabauy, Miami, FL (US)

(72) Inventor: Peter Cabauy, Miami, FL (US)

(73) Assignee: City Labs, Inc., Homestead, FL (US)

( * ) Notice: Subject to any disclaimer, the term of this patent is extended or adjusted under 35 U.S.C. 154(b) by 172 days.

(21) Appl. No.: 14/304,687

(22) Filed: Jun. 13, 2014

(65) Prior Publication Data
US 2014/0370332 A1    Dec. 18, 2014

Related U.S. Application Data

(60) Provisional application No. 61/834,671, filed on Jun. 13, 2013.

(51) Int. Cl.
| | |
|---|---|
| *H01M 10/46* | (2006.01) |
| *G21H 1/06* | (2006.01) |
| *H01M 10/052* | (2010.01) |
| *A61N 1/378* | (2006.01) |
| *H01M 10/0562* | (2010.01) |

(52) U.S. Cl.
CPC ............ *H01M 10/46* (2013.01); *A61N 1/378* (2013.01); *G21H 1/06* (2013.01); *H01M 10/052* (2013.01); *H01M 10/0562* (2013.01); *H01M 2220/30* (2013.01)

(58) Field of Classification Search
None
See application file for complete search history.

(56) References Cited

U.S. PATENT DOCUMENTS

| | | | | |
|---|---|---|---|---|
| 3,924,137 | A * | 12/1975 | Alger | H05H 6/00 376/108 |
| 2007/0088394 | A1* | 4/2007 | Jacobson | A61N 1/3925 607/4 |
| 2007/0088396 | A1 | 4/2007 | Jacobson | |
| 2012/0101540 | A1* | 4/2012 | O'Brien | A61B 5/0031 607/9 |
| 2013/0033149 | A1* | 2/2013 | Thomas | G21H 1/06 310/303 |

OTHER PUBLICATIONS

Honsberg, et al., GaN betavoltaic energy converters, Jan. 2005, IEEE photovoltaics specialist conference, 1-4.*
Kavetskiy et al., Tritium battery with solid dielectric, 2011, nuclear science and engineering, 168, 172-179.*

\* cited by examiner

*Primary Examiner* — Daniel Gatewood
(74) *Attorney, Agent, or Firm* — Beusse, Wolter, Sanks & Maire, PLLC; John DeAngelis

(57) ABSTRACT

A betavoltaic power source. The power source comprises a source of beta particles, one or more regions for collecting the beta particles and for generating electron hole pairs responsive thereto, and a secondary power source charged by a current developed by the electron hole pairs.

19 Claims, 2 Drawing Sheets

SMALL FORM FACTOR BETAVOLTAIC BATTERY FOR MEDICAL IMPLANTS

CROSS REFERENCE TO RELATED APPLICATIONS

The present invention claims priority under 35 U.S.C. 119(e) to the provisional patent application filed on Jun. 13, 2013 and assigned application No. 61/834,671. This provisional patent application is incorporated in its entirety herein.

FIELD OF THE INVENTION

The present invention applies to small form factor betavoltaic batteries especially for use with medical implants and in other applications where a small form factor is desired.

BACKGROUND OF THE INVENTION

Efforts aimed at miniaturization have always been a strong component associated with the advancements in the medical device/implant industry. In the $21^{st}$ century, this trend continues to be ever-present with a drive to scale down devices from a cubic centimeter range down to a cubic millimeter range. Smaller scale medical devices demonstrate great potential for reducing healthcare costs and mitigating trauma associated with invasive implant surgeries, while concomitantly improving both post-operative medical evaluations and convalescence periods.

The benefits of miniaturization are demonstrated with the emergence of a new class of cardiac pacemaker devices that are small enough to be inserted directly into a patient's right ventricle. The size reduction of these pacemakers and other medical devices is limited, in part, by the power sources that fuel the device's operation. Pacemaker batteries typically consume up to 40-80% of the device's volume. Consistent with this notion, further significant reductions in the scale of medical devices have been limited by the power sources themselves. While device components and electronic circuitry can be reduced to ever more diminutive dimensions, battery technology has traditionally remained limited to cubic centimeter dimensions arising as a consequence of exponential losses in energy density and capacity as batteries approach cubic millimeter scales. However, recent advancements in both electronics and battery technologies have led to reduced system power demands and higher power outputs from more diminutive power solutions.

Recent academic teams have laid the groundwork for an implantable cubic millimeter-scale device that can measure a glaucoma patient's intra-ocular eye pressure. This tiny device comprises a CMOS microcontroller that contains an on-board radio transmitter and sensor with cubic millimeter dimensions. The device operates at ultra-low power levels, e.g. picowatt power range during sleep cycles and at approximately microwatt power range during operational periods. Due to the extremely small dimensions of the device, it can be directly implanted within a patient's eye. The device can measure/record intra-ocular pressure throughout the day and radio-transmit processed data at periodic intervals to an external device for analysis.

This millimeter scale device utilizes an exceedingly small-sized solar cell to trickle-charge a millimeter scale LiPON (lithium phosphorous oxynitride) battery to provide a rechargeable power source. Such LiPON batteries are available from Cymbet Corporation of Elk River Minn., a manufacturer of small thin film, solid state secondary batteries. The Cymbet LiPON battery has approximately a 1 to 50 microamp-hour capacity, and the duty cycle of the device allows it to operate indefinitely as long as the solar cell provides an average of 10 nanoamps of current to the LiPON battery.

This configuration is well-adapted to an ocular implant where visible spectrum light energy is easily accessible and can be transmitted through the eye thereby providing the solar cell with the necessary trickle-charge power for the LiPON battery. However, such a solution is not suitable for implants that are not accessible to visible light, thereby rendering the solar cell component moot. An example of such a scenario might be a sensor embedded within a tumor for measuring pressure changes associated with tumor growth.

It should be noted that the LiPON battery can at best provide a maximum of 28 days of operation for implants in a stand-alone operation; this is far too short for most implantable devices that are not accessible to visible light sources. Clearly, a long-term (light-independent) trickle-charging source is required for maintaining the LiPON battery and subsequently facilitating operational effectiveness of such small scale sensor systems operating with such a LiPON battery.

Unfortunately, chemical batteries with less than cubic centimeter dimensions have a less than optimal energy density. The optimal energy density for a lithium iodide battery in conventional pacemakers is approximately 1 watt-hour per cubic centimeter with a volume greater than about 3.0 cubic centimeters. To supply sufficient power to shrinking medical devices, an energy density of greater than about 1 watt-hour per cubic centimeter is desirable for battery volumes of approximately 0.5 cubic centimeters or less. In battery volumes of 0.1 cubic centimeters, a 10 watt-hour per cubic centimeter energy density would be highly desirable due to the loss of energy capacity in such a small volume (i.e. 1 watt-hour of capacity in a tenth of a cubic centimeter).

Furthermore, the battery needs to provide power in ranges from nanoamps to milliamps to accommodate duty cycle power requirements of medical device electronics. For example, wireless signals (to transmit the sensed values to an external device) require higher power bursts for short durations while the microcontroller's sleep power provides a low, but continuous drain. An ideal medical implant power source will have a high energy density that is robust under a wide-range of power drains while having a diminutive form factor. Unfortunately, currently available betavoltaic power sources with less than 1 cubic centimeter dimensions will have only nano-watt to low-microwatt power outputs falling short of the required, or at least desired, higher power output necessary in some medical implant functions (e.g. radio telemetry, defibrillation etc.).

Historically, betavoltaic power sources for medical device implants are not a new concept as they have a demonstrated potential for high energy densities well beyond conventional chemical batteries. Betavoltaic power sources do, however, suffer from low power densities and radiation shielding requirements. In the early 1970's, a group of researchers at Donald W. Douglas Laboratories of Richland, Wash. (led by Dr. Larry Olsen) invoked a promethium-147 radio-isotope to fuel a betavoltaic power source (also referred to as a Betacel) for energizing a cardiac pacemaker, which was successfully implanted in over 100 patients. Although the Betacel's size approximated 1.0 cubic inch due to shielding requirements incurred from an associated gamma radiation emitting promethium-146 component, the successful implementation of this technology demonstrated the feasibility of betavoltaics for use within medical implants.

BRIEF DESCRIPTION OF THE FIGURES

The foregoing and other features of this invention will be apparent from the following more particular description of the invention, as illustrated in the accompanying drawings, in which like reference characters refer to the same parts throughout the different figures.

DETAILED DESCRIPTION OF THE INVENTION

Figure 1:
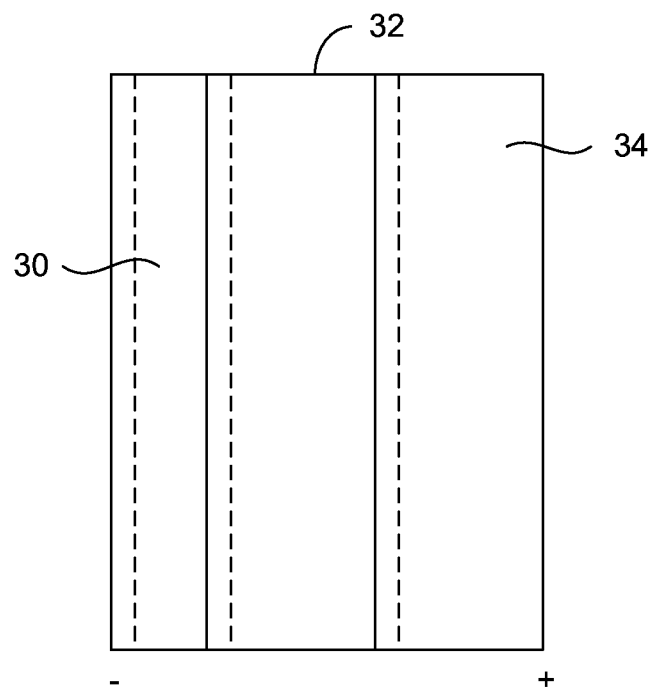
FIG. 1 illustrates a triple junction for use with the present invention.

In the teachings of the various embodiments of this invention, miniature betavoltaic power sources (with dimensions ranging from about a cubic millimeter to approximately 0.5 cubic centimeters) are constructed with energy densities approximately ranging from about 1 watt-hour per cubic centimeter to about 500 watt-hours per cubic centimeter. The energy density for a betavoltaic power source is calculated by integrating the betavoltaic device's power density over the medical device's useful life (e.g. 10 years for pacemakers). Betavoltaic power sources can be constructed in cubic millimeter volume spaces without affecting the energy density; this is unlike conventional chemical battery technology where practical limitations exist in constructing micro-scaled cathodes, anodes, and liquid electrolyte volumes without incurring losses in energy density.

In the case of promethium the inventor has discovered that the removal of the Pm-146 component is an important factor in reducing the shielding requirements for the betavoltaic battery. The gamma of Pm-146 is very high energy and is difficult to shield. The resulting shield requirements after removing the Pm-146 component are considerably less than the original BetaCel, as described above, that had the Pm-146 component with the Pm-147 component.

Tritium beta flux can be shielded with a thin sheet of paper but tritium betavoltaic power sources of the prior art have been too low for use as a power source for medical electronics. It is only with the thinning of InGaP cells, new high tritium density metal tritide films and/or the use of enhanced surface area semiconductors, as described herein or in the referenced commonly-owned patent applications, that the inventor has been able to approach energy densities of 1 watt-hour/cm^3 or greater and power densities in the range of 10's to 100's of microwatts/cm^3.

Betavoltaic power sources are typically comprised of a beta-emitting radioisotope affixed directly onto a semiconductor collector that is packaged in a container, which provides radiation shielding to levels appropriate for the intended application. The semiconductor collector material is similar to a solar cell and can easily be miniaturized to micro-scales without exhibiting losses in electrical properties. Furthermore, radioisotopes such as tritium (H-3), promethium-147 (Pm-147), and nickel-63 (Ni-63) can all be incorporated into metallic forms, which can be similarly scaled to the semiconductor collector's dimensions.

In one embodiment of this invention, a betavoltaic power source with a volumetric dimension of approximately 0.5 cubic centimeters or less outputs power in the nano-watts to microwatts range and can provide nominal power in standby or active modes to medical implant circuitry.

In another embodiment of this invention, a betavoltaic power source with a volumetric dimension of approximately 0.5 cubic centimeters or less outputs power in the nano-watts to microwatts level and can provide nominal power in standby or active modes to the medical implant circuitry while utilizing a portion of its generated power to trickle charge a secondary battery and/or a capacitor and/or another energy storage device. The secondary battery and/or capacitor and/or other energy storage device is capable of modulating interim power that at times may be higher than the standalone betavoltaic power supply (e.g. power bursts for radio telemetry, defibrillation etc.).

In yet another embodiment of this invention, a betavoltaic power source with a volumetric dimension of approximately 0.5 cubic centimeters or less outputs power in the nano-watts to microwatts level and can provide nominal power in standby or active modes to the medical implant circuitry while utilizing a portion of its power to trickle charge a secondary battery and/or a capacitor and/or another energy storage device with volumetric dimensions of approximately 0.5 cubic centimeters or less. The secondary battery and/or capacitor and/or other energy storage device is capable of modulating interim power that may be higher than the standalone betavoltaic's power supply (e.g. power bursts for radio telemetry, defibrillation etc.).

In one embodiment of this invention, a Pm-147-based betavoltaic power source with a volume that is less than approximately 0.5 cubic centimeter is constructed. The Pm-147 betavoltaic can be hermetically sealed within a cylindrical form factor (or another form factor appropriate for the intended application) that, in turn, allows currently available medical device delivery systems (e.g. catheters, stent delivery systems, syringe, etc.) to implant these device in vivo. The seal may comprise a bio-inert stainless steel package with a seam sealer, resistance welder, ultrasonic welder or laser-welder. The bio-inert package can be made with ceramic and/or metal materials known in the art.

The Pm-147 isotope is made free of Pm-146 via current methods known in the art (e.g., see U.S. Pat. No. 7,435,399) allowing for modest radiation shielding requirements (e.g. use of a biocompatible metals/materials sufficient for shielding). This is in stark contrast to the original Betacel Pm-147, as described above, betavoltaic power supply for cardiac pacemakers that required considerable shielding due to the concomitant Pm-146 component.

In addition, the Pm-147 can be made into a bidirectional radiation source using methods known in the art. The semiconductor collector (e.g. a pn junction) may be constructed from silicon material or may from other semiconductor materials known in the art (GaAs, GaP, InGaP, GaN, SiC etc).

In one example, the semiconductor collector comprises a type III-V material such as GaAs. GaAs has a relatively high diffusion length for its minority carriers but still requires multiple junctions to be grown in order to capture the majority of the electron-hole pairs (EHPs) generated via the beta particles impinging on the semiconductor collector.

FIG. 1 illustrates a triple-junction device (three pn regions 30, 32 and 34) where EHPs may be collected throughout the collector's volume. Each junction can be made between 15-20 microns thick or in appropriate dimensions that optimize the collection efficiency. It is estimated that Pm-147 beta particles can travel approximately 60 microns or more into a GaAs semiconductor. Optimization of the junction thickness and the number of junctions can be made for different semiconductor collector material. The vertical dashed line in FIG. 1 denotes the boundary of a p and an n region; the larger region illustrated in FIG. 1 can be either the p region or the n region.

In another embodiment of a Pm-147 betavoltaic, two triple junction GaAs collectors are constructed with a Pm-147 bidirectional source in the middle forming a unit. Both triple junctions are placed in intimate contact with Pm-147 source and are electrically connected in parallel. The GaAs triple junction collector has circular dimensions with a diameter of about 0.4 centimeters and a thickness of about 120 microns. Each p/n region forms a junction so three p/n regions form a triple junction. This technique is used in solar cells today in order to capture different wavelengths of light based on their penetration depth into solar cells.

Figure 2:
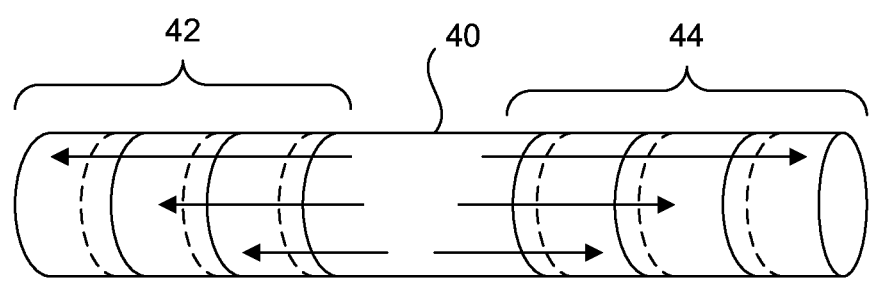
FIG. 2 illustrates a bi-directional betavoltaic cell

FIG. 2 illustrates such a device with a source 40 between triple junctions 42 and 44. Each junction is approximately 15-20 microns thick and the Pm-147 bidirectional source is approximately 6 milligrams per square centimeter at 400 Curies per gram or 2.4 Curies per square centimeter. The combined bidirectional unit of FIG. 2 comprises 1.0 square centimeter and yields an open circuit voltage of 2.4 volts and a short circuit current of 14 microamps generating approximately 27 microwatts of power at beginning-of-life (BOL) with a fill-factor of approximately 80 percent. The half-life of Pm-147 is approximately 2.62 years and it should be noted that many medical devices have a useful lifetime of 3-5 years thereby permitting use of a Pm-147 device.

Note that the thickness of the individual regions within the triple junctions 42 and 44 are greater at increasing distance from the source 40 to account for the exponential decay of the beta particle flux. The arrowheads represent the beta particle flux. Generally, the thickness of the individual regions is selected so that about the same current is produced within each individual region. The individual regions (or cells since each region produces a current) within the triple junction 42 are in series and the individual regions within the trip junction 44 are in series. But the triple junctions 42 may be connected in series or in parallel with the triple junctions 44. The FIG. 2 embodiment is shown in an elongated representation; in another embodiment the source 40 and the junctions 42 and 44 are each shorter and thus the combination is more disc-like than the tubular representation of FIG. 2.

The power density for this betavoltaic device 40 is approximately 5 milliwatts per cubic centimeter with an energy density of approximately 125 Watt-hours per cubic centimeter when integrated over two half-lives (5.24 years). In order to modulate the power outputs from the Pm-147 betavoltaic source, two bidirectional units may be placed in series in order to yield an open circuit voltage of 4.8 Volts with a short circuit current of 14 microamps at BOL. The two bidirectional units may be connected to a LiPON battery, and/or capacitor and/or energy storage device configuration in order to receive a trickle charge and subsequently discharge/modulate higher power over a duty cycle or on-demand. By combining one or more LiPON batteries within a small millimeter scale volume, the power emanating from the Pm-147 betavoltaic units can be modulated freely from the nanoamp up to the maximum current output (e.g. Amp-seconds). The approximate dimensions for this assembly, comprising two bidirectional Pm-147 sources, four betavoltaic collectors, and the LiPON batteries, is 0.05 cubic centimeter.

Rechargeable thin-film LiPON batteries may be purchased from Cymbet Corporation of Elk River, Minn. or Infinite Power Solutions from Littleton, Colo. LiPON batteries are robust over 10,000 charge/discharge cycles and have a low discharge rate of 3-6% even at human body temperatures. LiPON batteries can be discharged at rates of 10 C (capacity) and in short bursts up to 40 C without deleterious effects upon its capacity or performance. For instance, in the case of a battery with 50 microamp-hour capacity it is possible to discharge at 1 C. This would be a 1 hour discharge at a rate of 50 microamps continuous. Or it can be discharged at 40 C for a short period, resulting in a rate of 2 milliamps.

Cymbet Corporation's LiPON batteries can be fabricated with form factors well within cubic millimeter dimensions and with energy capacities of 1-50 microamp-hours. Infinite Power Solutions' batteries have capacities in the sub-milliamp-hour range, but they demonstrate a larger form-factor with linear dimensions measuring in the centimeter range and thicknesses of 180 microns. However, they are malleable enough to conform to cylindrical shapes. It should be noted that custom LiPON batteries with various dimensions and capacities can also be fabricated as desired.

In another embodiment, a tritium-based betavoltaic collector cell involving a III-V semiconductor, such as the structures described in the commonly-owned U.S. Pat. No. 8,487,507, entitled Tritium Direct Conversion Semiconductor Device and incorporated herein by reference, is utilized. In one embodiment the dimensions are approximately 0.5 cm×0.5 cm or smaller per betavoltaic collector layer. Other embodiments may have larger dimensions. Additionally, the betavoltaic layers may be constructed with an approximate 0.5 cm diameter or smaller in order to optimally fit into a cylindrical medical devices that can be implanted via a catheter-like delivery system. The thickness of the betavoltaic cell is approximately 10-25 microns or less with a tritium metal tritide layer (e.g. titanium, scandium, magnesium, lithium, palladium, etc.) having a thickness approximately ranging from less than 100 nanometers to greater than 1.0 micron, that is placed in contact with the active surface of the betavoltaic cell.

This is a thin III-V betavoltaic cell that utilizes an epitaxial-lift-off process or etching away of the substrate coupled with a back metallization to offer conduction and support of the cell. Additionally, the thin III-V betavoltaic cell may use a metal tritide layer as back metallization via the deposition of candidate metal tritide forming metals or combination of metals as listed above. These metals may be deposited through evaporation, sputtering or other methods known in the art. The metal tritide back metal offers support to the thin betavoltaic cell and an additional source of beta-flux through the back-side of the betavoltaic cell; thereby increasing electron-hole pair generation and the overall production of electrical power. It should be noted that the metal tritide metal may in some instance be insulating due to the tritium in the metal matrix. In such cases, a portion of the back side metal may be a conductive non-hydriding forming metal so as to provide electrical conduction for the betavoltaic cell. In order to achieve reasonable power densities the cells are stacked in series and parallel with the aid of flexible circuit cards or other interposers between some of the layers to make parallel connections or even series connections.

The betavoltaic cell may also have thicknesses ranging from approximately 25 microns to 625 microns. For thicker betavoltaic cells (e.g. 25 microns to 625 microns or greater), the inventors propose to use a surface enhancement technique to raise the power density/energy density. Although, surface enhancement techniques may also be utilized in thinner betavoltiac cells (e.g. 25 microns or thinner).

Another approach that may be used is to thin the back surfaces of the betavoltaic semiconductor substrates by etching, polishing, grinding, and/or other lapidary techniques known in the art. The scandium, titanium, magnesium, palladium, lithium, or other suitable tritide forming layer may be metallurgically placed on top of the betavoltaic cell by directly depositing on top of the betavoltaic cell's active area through methods known in the art (e.g. evaporation, electro-deposition, sputtering, etc.). Alternatively, the metal tritide layer may be deposited on a separate thin substrate (i.e. ~25 microns to ~500 microns) that is mechanically connected to the betavoltaic cell's active area via pressure, epoxy, or spot welding.

In one embodiment the inventor prefers to have the tritide metal layer evaporated onto the cell's active area rather than to have a separate substrate. This allows the formation of a single monolithic piece that includes both the metal tritide and the betavoltaic collector. In another embodiment a betavoltaic cell comprises two separate components (betavoltaic collector and tritium metal tritide layer/foil), but generally this embodiment occupies more volume and is lower in both power and energy density.

The metal tritide is formed by exposure to tritium gas at pressures approximately ranging from less than 0.01 to greater than 20 Bar and temperatures ranging approximately room temperature to 600° C. for durations ranging minutes to days. A cap layer of palladium ranging from approximately 1.0 nanometer to 500.0 nanometers may be deposited over a scandium, titanium, magnesium, lithium, or other suitable metal in order to reduce the tritium loading temperature and stabilize the tritium within the metal matrix after the tritide has been formed. The palladium cap layer functions primarily as a catalyst and serves to provide for an expedited rate of reaction for inducing the process of tritiation; palladium has an additional benefit for the tritiation process in that it can facilitate tritium loading of a metal tritide at significantly lower temperatures and pressures compared to processing efforts conducted in the absence of palladium. This subsequent increase in the kinetics of the tritiation process induced by the palladium cap layer does not alter the ultimate functionality of the betavoltaic cell, and it is usually deposited directly upon un-passivated surfaces (surfaces containing no oxide barriers to tritiation) of metal hydride storage layers (e.g. scandium, titanium, magnesium, lithium, or other suitable metal). The palladium layer is typically laid down in a vacuum/inert gas atmosphere process, in order to eliminate oxygen contamination and is deposited via any of the metal deposition techniques described elsewhere herein. It should also be noted that the metal tritide layer may also be formed via an in-situ evaporation of the metal in the presence of gaseous tritium.

The average current produced in a type III-V semiconductor in the presence of the metal tritide is approximately 1.0 to 6.0 nanoamps per square millimeter or 100-600 nanoamps per square centimeter. The open circuit voltage for a type III-V structure ranges between 0.4 Volts to 1.2 Volts.

Betavoltaic cell layers may be stacked vertically and configured in series or parallel utilizing through-vias as power lead contacts across betavoltaic cell layers or by using current-channeling interposers (e.g. flexible circuit cards or yttria-stabilized zirconia dielectric materials) in between betavoltaic cells or groups of cells. It should be noted that various stacking configurations (serial, parallel, combination) produce different voltage and current outputs from the betavoltaic composite device.

In one example, a tritium betavoltaic device is comprised of 10 micron thick betavoltaic cell layers with through-vias for electrical connections. Each betavoltaic cell consists of a type III-V semiconductor material as described in the commonly-owned U.S. Pat. No. 8,487,507 and entitled Tritium Direct Conversion Semiconductor Device and a tritium metal tritide deposited on its surface producing a short-circuit current of about 300 nanoamps per square centimeter at BOL (beginning of life) and a voltage of 0.9 volts per cell layer with a fill-factor of approximately 80%. The composite betavoltaic device can be made with a variety of form factors ranging from cubic millimeter volumes or greater and varying geometries (e.g. cylindrical). The power density is approximately 216 microwatts per cubic centimeter at BOL and 15 Watt-hours per cubic centimeter when integrated over one tritium half-life (12.3 years).

The application sets forth example dimensions for a betavoltaic source and its constituent elements. However, variations from the recited dimensions provide useful sources with desirable operating properties. For example, a 150 micron thick cell may still be useful in certain applications. For example, a commonly-owned provisional patent application assigned application No. 61/838,692 filed on Jun. 23, 2014 describes enhanced surface area cells. In this case, the cell may be 150 microns thick but it may have an effective area of 10× due to valleys/trenches of the enhanced surfaces as described in the aforementioned provisional application, which is incorporated herein.

Similar to the Pm-147 betavoltaic embodiment, a 1-50 microamp-hour LiPON secondary thin-film battery may be connected to the composite tritium betavoltaic device in order to modulate freely from nanoamp to milliamp ranges. Furthermore, other secondary battery, capacitor and/or energy systems may be utilized. This hybrid betavoltaic comprised of tritium betavoltaic layers that trickle charge a LiPON battery and/or capacitor and/or energy storage systems can be used to power leadless pacemakers requiring average continuous power draw of approximately 5-30 microwatts for over 12 years within a volume of approximately 0.1 cubic centimeters. This represents a factor-of-ten reduction in volume being approximately one tenth the size of the smallest leadless pacemaker batteries currently in existence today without sacrificing energy density, capacity, or power output performance.

The application sets forth example dimensions for various betavoltaic sources and their constituent elements. However, variations from the recited dimensions provide useful sources with desirable operating properties. For example, a hybrid betavoltaic power source with 0.5 cubic centimeters or greater may be desired in certain applications. For instance, a small betavoltaic source with secondary energy systems that may be larger than 0.5 cubic centimeters are useful in certain applications.

In another example, this composite tritium betavoltaic's form factor may be constructed with dimensions of 1.5 mm×2.0 mm×0.15 mm producing 0.1 microwatts of power at BOL and can easily trickle-charge a 1.0 microamp-hour LiPON battery measuring 1.5 mm×1.3 mm×0.15 mm. This small form factor hybrid tritium betavoltaic can supply an ultra-low power microcontroller with a pressure sensor such as the implantable cubic millimeter ocular-implant wireless pressure sensor for glaucoma patients described above.

The hybrid tritium betavoltaic may be physically bonded to the cubic millimeter wireless pressure sensor comprising a microcontroller, memory, analog-digital converter, pressure sensor, and wireless transceiver to achieve a cubic millimeter scale device structure.

Figure 3:
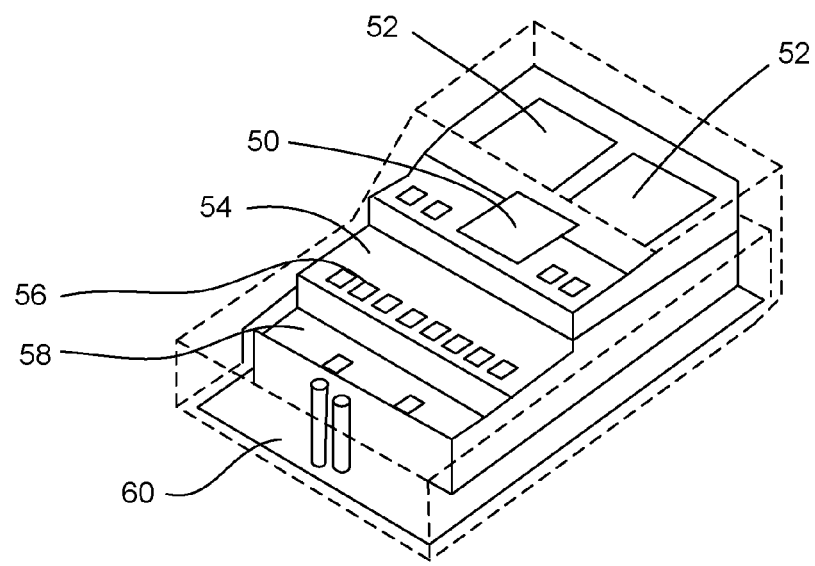
FIG. 3 illustrates use of a betavoltaic battery in an implantable device.

FIG. 3 illustrates such a device comprising a hybrid tritium betavoltaic 50, a wireless transceiver 52 for sending a receiving signals from an external device, an ND and/or D/A converter 54, a processor and memory elements 56, a chargeable power source 58, and a MEMS pressure sensor 60. In one embodiment the structure of FIG. 3 is about 0.5 mm×2 mm×1.5 mm.

The hybrid tritium betavoltaic source supplies power and energy capacity for operating in any area of the body for over a decade without the need for light collected via a solar cell. As a note, the invention is not limited to the cubic millimeter volume set forth in FIG. 3 and can be made using other ultra-low power cubic millimeter devices known in the art. Applications are also not limited to pressure and temperature sensing but can make use of other ultra-low power sensing devices. In addition, it can be used for therapeutic purposes such as dispensing medication from an on-chip dispenser that can be implanted in strategic medical locations. It should be noted that cubic millimeter scale ultra-low power devices can vary in power consumption depending on configuration, duty cycle and sensor capabilities. However, the hybrid tritium-based betavoltaic can meet varying current and voltage requirements via stacking and electrical connection configurations. Similar betavoltaics with higher power in the range of microamps may be made with other radioisotopes such as Pm-147.

The hybrid tritium betavoltaic coupled to the pressure sensor of FIG. 3 can also be used in non-medical, external environments such as in mesh sensor networks (e.g. Dust networks). It can also be used in conjunction with radioactive implantable seeds that irradiate tumors. This system can provide daily monitoring of a tumor and can provide information of the tumor's size change via changes in pressure. This approach can also be used with chemotherapy in-lieu of the radioactive seed. This type of wireless sensor can also be used in stents to measure pressure/strain changes that would actively monitor scar-tissue growth.

In another embodiment, the semiconductor collector's surface may be enhanced to increase the surface area of the collector. An increase in surface area provides an increase in power production ranging from approximately 2 to 100 times the power produced from a planar surface betavoltaic semiconductor collector. Semiconductor collector surface structures with increased surface area and power production are described in a related and commonly owned provisional patent application filed on Jun. 24, 2013 and assigned application No. 61/838,692.

In all embodiments, the radioisotope may be exchanged for other beta-emitting radioisotopes known in the art. Radioisotope selection can be made to optimize power vs longevity and/or cost or availability. For example, Phosphorus-33 is a short lived beta-emitting radio-isotope with a half-life of 25.,3 days and has an energy spectrum that approximates that of Promethium-147. The advantage over Promethium-147 is that it is readily available and less expensive and may be appropriate for certain short-lived applications (e.g. short-lived medical implant sensors).

The increased surface area of the semiconductor collector may be used with or without the thin semiconductor epi-layers described in this patent application and in the commonly-owned patent application assigned application Ser. No. 12/637,735 and filed on Dec. 14, 2009. Increased surface area semiconductor collectors can increase the energy density of betavoltaics by up to 100 times or greater over planar semiconductor surfaces. Additionally, the enhanced surface area reduces the overall cost of betavoltaic devices by reducing the semiconductor area necessary to power devices.

According to the certain embodiments of the present invention, it comprises one or more beta sources coupled to betavoltaic collectors. The arrangement can be as simple as a two-dimensional beta source and betavoltaic collector connected to a secondary battery, and/or capacitor, and/or any other secondary energy storage unit. In another configuration, the beta sources/collectors can be configured in series or parallel to trickle charging the secondary cell or battery with the secondary cell or battery for use during power bursts or modulations. The betavoltaic cell or battery can also utilize a portion of its power to supply electrical systems without the aid of the secondary energy storage unit.

Figure 4:
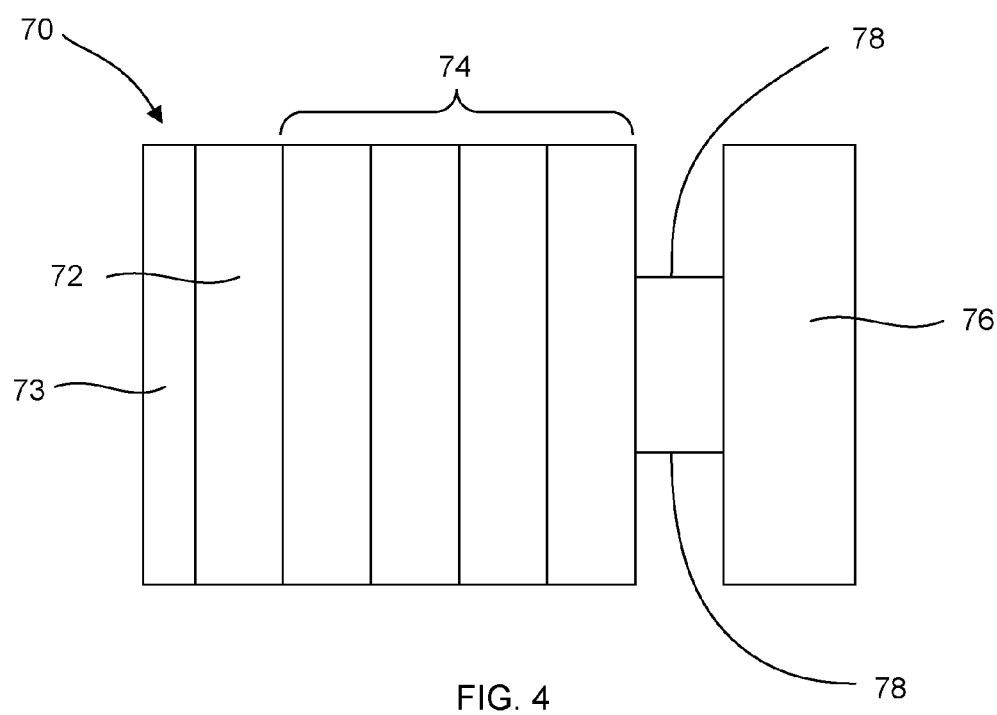
FIG. 4 illustrates a betavoltaic battery of the present invention.

FIG. 4 illustrates a betavoltaic battery 70 comprising a source of beta particles 72, regions 74 for collecting the beta particles, and secondary power source 76 charged by the electron-hole pairs generated within the region 74. In some embodiments, a palladium material layer 73 is disposed proximate a first surface of the source of beta particles 73, where the regions 74 for collecting the beta particles are proximate a second surface of the source of beta particles 72, the first and second surfaces on opposing sides of the source of beta particles 72. However, in other embodiments, the palladium material layer 73 is excluded. In the illustrated embodiment the secondary power source is connected to the regions 74 via conductors 78. In another embodiment (not illustrated) the secondary power source 76 is bonded to or in intimate contact with the regions 74 in lieu of utilizing the conductors 78.

Note that palladium can also form a metal tritide. However, it does not have as high a tritium content as, for example, a titanium tritide, scandium tritide, magnesium tritide, lithium tritide etc. However, the palladium cap layer prevents oxidation of the titanium, scandium, magnesium or lithium metal below it since these metals will readily oxidize and form an oxide barrier to tritium when exposed to air. It also dissociates the T2 (tritium two) molecule to elemental T allowing it to diffuse and bond to the metal hydride below it (e.g. titanium, magnesium, lithium, scandium etc.). The palladium also helps keep the tritium in the metal hydride below because it prevents oxygen from attacking the metal and releasing tritium species (e.g. tritium oxides, tritium metal oxides) into the surrounding environment. This makes the palladium useful when handling the tritium sources post-tritiation. It is helpful in the manufacturing process because of reduced tritium contamination.

While certain embodiments of the present invention have been shown and described herein, such embodiments are provided by way of example only. Numerous variations, changes and substitutions will occur to those of skill in the art without departing from the invention herein. Accordingly, it is intended that the invention be limited only by the spirit and scope of the appended claims.

What is claim is:
1. A betavoltaic power source comprising
   a source of beta particles;
   one or more regions comprising semiconductor material for collecting the beta particles and for generating electron hole pairs responsive thereto; and
   a secondary power source charged by a current developed by the electron hole pairs;
   wherein the betavoltaic power source has a volumetric dimension of 0.5 cubic centimeters or less.

2. The betavoltaic power source of claim 1 wherein the source of beta particles comprises tritium (H-3), promethium-147 (Pm-147), or nickel-63 (Ni-63).

3. The betavoltaic power source of claim 1 wherein the source of beta particles comprises a tritium metal tritide material.

4. The betavoltaic power source of claim 1 wherein the secondary power source comprises a secondary battery, a capacitor or an energy storage device.

5. The betavoltaic power source of claim 1 wherein the one or more regions comprise GaAs.

6. The betavoltaic power source of claim 1 wherein the source of beta particles is disposed between a first and a second region for collecting the beta particles.

7. The betavoltaic power source of claim 1 wherein the secondary power source comprises a LiPON battery.

8. The betavoltaic power source of claim 1 for use in an implantable medical sensor or a medical device.

9. The betavoltaic power source of claim 1 further comprising a palladium material layer disposed proximate a first surface of the source of beta particles, wherein the one or more regions are proximate a second surface of the source of beta particles, the first and second surfaces on opposing sides of the source of beta particles.

10. The betavoltaic power source of claim 1 wherein the source of beta particles comprises a tritium metal tritide material layer.

11. The betavoltaic power source of claim 10 wherein the tritium metal tritide material layer comprises one or more of scandium, titanium, magnesium, palladium, and lithium.

12. The betavoltaic power source of claim 10 further comprising a palladium material layer disposed on a surface of the tritium metal tritide material layer.

13. The betavoltaic power source of claim 10 wherein an amount of tritium in the metal tritide material layer is selected to achieve a desired power level or energy density.

14. A betavoltaic power device comprising a plurality of betavoltaic power sources of claim 1.

15. The betavoltaic power source of claim 1 wherein one or more of the regions for collecting the beta particles and for generating electron hole pairs responsive thereto comprises a respective thickness based on a flux of the beta particles in each respective region.

16. The betavoltaic power source of claim 1 wherein the semiconductor material comprises at least one p-n junction and wherein the semiconductor material is type III-V semiconductor material.

17. The betavoltaic power source of claim 1 wherein a respective thickness of the one or more regions is based on a distance between the respective region and the source of the beta particles.

18. The betavoltaic power source of claim 1 wherein the source of beta particles comprises promethium-147 (Pm-147) and excludes promethium-146 (Pm-146).

19. The betavoltaic power source of claim 1 having an energy density in a range from 1 watt-hour per cubic centimeter to 500 watt-hours per cubic centimeter, wherein the energy density is calculated by integrating the betavoltaic power source power density over a lifetime of the power source.

* * * * *